(12) United States Patent
Naunheimer et al.

(10) Patent No.: US 7,718,146 B2
(45) Date of Patent: May 18, 2010

(54) ENHANCED BED SEPARATION IN A STYRENE MONOMER REACTOR USING MILLED PLATES

(75) Inventors: Christopher Naunheimer, Arlington Heights, IL (US); Paul A. Sechrist, South Barrington, IL (US); Michael A. Schultz, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 226 days.

(21) Appl. No.: 12/119,566

(22) Filed: May 13, 2008

(65) Prior Publication Data

US 2009/0285729 A1 Nov. 19, 2009

(51) Int. Cl.
*B01J 8/04* (2006.01)
*B01J 8/02* (2006.01)
*B01J 8/44* (2006.01)

(52) U.S. Cl. ........ 422/190; 422/192; 422/211; 422/218; 422/220; 422/239; 422/311

(58) Field of Classification Search ........ 422/190, 422/192, 211, 218, 220, 239, 311
See application file for complete search history.

(56) References Cited

U.S. PATENT DOCUMENTS

| | | | | |
|---|---|---|---|---|
| 2,634,194 A * | 4/1953 | Nebeck | 422/218 |
| 3,480,406 A | 11/1969 | Luckenbach | 23/288 |
| 4,021,499 A | 5/1977 | Bieser | 260/674 SA |
| 4,036,779 A | 7/1977 | Schatz et al. | 252/417 |
| 4,079,094 A | 3/1978 | Rosback et al. | 260/674 SA |
| 4,096,911 A * | 6/1978 | Geske | 166/234 |
| 4,108,915 A | 8/1978 | Rosback et al. | 260/674 SA |
| 4,126,539 A | 11/1978 | Derr, Jr. et al. | 208/108 |
| 4,193,910 A | 3/1980 | Rohrbach et al. | 260/42.43 |
| 4,251,675 A | 2/1981 | Engel | 585/422 |
| 4,276,265 A * | 6/1981 | Gillespie | 422/311 |
| 4,421,723 A * | 12/1983 | Farnham | 422/218 |
| 4,435,279 A | 3/1984 | Busch et al. | 208/111 |
| 4,497,792 A | 2/1985 | Gindler | 424/3 |
| 4,567,022 A | 1/1986 | Greenwood | 422/144 |
| 4,721,603 A | 1/1988 | Krug et al. | 422/147 |
| 4,778,941 A | 10/1988 | Tagamolila | 585/319 |
| 4,971,771 A * | 11/1990 | Stahl | 422/218 |
| 5,089,115 A * | 2/1992 | Koves | 208/146 |
| 5,118,419 A * | 6/1992 | Evans et al. | 210/291 |

(Continued)

FOREIGN PATENT DOCUMENTS

GB 1128244 9/1968

OTHER PUBLICATIONS

U.S. Appl. No. 12/119,569, filed Nov. 19, 2009, Naunheimer et al.

(Continued)

*Primary Examiner*—Walter D Griffin
*Assistant Examiner*—Huy-Tram Nguyen
(74) *Attorney, Agent, or Firm*—Mark Goldberg

(57) ABSTRACT

An apparatus for use in radial flow reactors is presented. The apparatus includes a plate of sufficient thickness to impart strength in supporting a solid particle bed, and is milled to have narrow slots allowing the flow of fluid through the plate, while preventing the passage of catalyst through the plate.

17 Claims, 4 Drawing Sheets

U.S. PATENT DOCUMENTS

| | | | | |
|---|---|---|---|---|
| 5,156,738 A | * | 10/1992 | Maxson | 210/274 |
| 5,302,357 A | | 4/1994 | Kramer et al. | 422/219 |
| 5,380,426 A | | 1/1995 | Johnson et al. | 208/113 |
| 5,618,426 A | * | 4/1997 | Eischen et al. | 210/541 |
| 5,827,485 A | * | 10/1998 | Libal et al. | 422/179 |
| 6,096,937 A | | 8/2000 | Butler et al. | 585/440 |
| 6,106,702 A | | 8/2000 | Sohn et al. | 208/310 Z |
| 6,225,518 B1 | | 5/2001 | Sohn et al. | 585/826 |
| 6,612,731 B2 | | 9/2003 | Nishida et al. | 366/173.2 |
| 6,706,938 B2 | | 3/2004 | Roeseler et al. | 585/820 |
| 6,740,788 B1 | | 5/2004 | Maher et al. | 585/319 |
| 6,762,335 B1 | | 7/2004 | Prince et al. | 585/440 |
| 6,855,854 B1 | | 2/2005 | James, Jr. | 585/323 |
| 6,858,769 B2 | | 2/2005 | Woodle et al. | 585/658 |
| 6,894,201 B1 | | 5/2005 | Schmidt et al. | 585/448 |
| 7,094,939 B1 | | 8/2006 | Jeanneret | 585/323 |
| 7,105,711 B2 | | 9/2006 | Merrill | 585/266 |
| 7,118,715 B1 | | 10/2006 | Hedrick et al. | 422/144 |
| 7,128,826 B2 | | 10/2006 | Eldin et al. | 208/48 AA |
| 7,128,883 B2 | | 10/2006 | James, Jr. | 422/211 |
| 7,205,448 B2 | | 4/2007 | Gajda et al. | 585/823 |
| 7,226,568 B1 | * | 6/2007 | Ham et al. | 422/218 |
| 7,276,636 B2 | | 10/2007 | Jeanneret | 585/323 |
| 2008/0107575 A1 | * | 5/2008 | Vetter et al. | 422/211 |

OTHER PUBLICATIONS

U.S. Appl. No. 12/119,570, filed Nov. 19, 2009, Naunheimer et al.

* cited by examiner

ENHANCED BED SEPARATION IN A STYRENE MONOMER REACTOR USING MILLED PLATES

FIELD OF THE INVENTION

This invention relates to cross-flow reactors or adsorbers where a fluid flows across a moving bed of catalyst or adsorbent. In particular, this relates to the internal components for distribution flow of the fluid and for providing a device for preventing the flow of catalyst or adsorbent across the inlet or outlet screens.

BACKGROUND OF THE INVENTION

A wide variety of processes use radial flow reactors to provide for contact between a fluid and a solid. The solid usually comprises a catalytic material on which the fluid reacts to form a product. The processes cover a range of processes, including hydrocarbon conversion, gas treatment, and adsorption for separation.

Radial flow reactors are constructed such that the reactor has an annular structure and that there are annular distribution and collection devices. The devices for distribution and collection incorporate some type of screened surface. The screened surface is for holding catalyst beds in place and for aiding in the distribution of pressure over the surface of the reactor to facilitate radial flow through the reactor bed. The screen can be a mesh, either wire or other material, or a punched plate. For either a fixed bed or moving bed, the screen or mesh provides a barrier to prevent the loss of solid catalyst particles while allowing fluid to flow through the bed. In a moving bed, solid catalyst particles are added at the top, and flow through the apparatus and removed at the bottom, while passing through a screened-in enclosure that permits the flow of fluid over the catalyst. In a fixed bed, the catalyst, or adsorbent, is loaded into a bed between screens, or other retention devices, and the screens allow fluid to flow over the catalyst while holding the catalyst in place. The screen is preferably constructed of a non-reactive material, but in reality the screen often undergoes some reaction through corrosion, and over time problems arise from the corroded screen or mesh.

One type of screen is a profile wire screen, where a profile wire is wrapped around supports and set at a predetermined spacing for the wire as it is wrapped around the supports. The screen is then cut and flattened and then re-rolled or re-shaped. The screen is shown in U.S. Pat. No. 2,046,458 and U.S. Pat. No. 4,276,265. The screen can be used as part of an inlet distribution device, or other device for containing a catalyst. One type of inlet distribution device is a reactor internal having a scallop shape and is described in U.S. Pat. No. 6,224,838 and U.S. Pat. No. 5,366,704. The scallop shape and design provides for good distribution of gas for the inlet of a radial flow reactor, but uses screens or meshes to prevent the passage of solids. The scallop shape is convenient because it allows for easy placement in a reactor without concern regarding the curvature of the vessel wall. The screens or meshes used to hold the catalyst particles within a bed are sized to have apertures sufficiently small that the particles cannot pass through.

The design of reactors to overcome these limitations can save significantly on downtime for repairs and on the loss of catalyst, which is a significant portion of the cost of processing hydrocarbons.

BRIEF SUMMARY OF THE INVENTION

The present invention provides for a new screen design that provides greater strength and reduces the failure of a reactor during operation. In particular, the design provides greater integrity for preventing the passage of solid particles through the screen for a radial flow reactor. The invention comprises a reactor having two reactor beds for performing separate functions. The apparatus comprises a first partition having a first radius and forming an inner pipe, wherein the inner pipe allows for flow of fluid through the pipe, and a second partition having a radius greater than the first radius and forming a cylindrical structure surrounding the first partition. A first solid particle catalyst bed is disposed between the first and second partitions, and the partitions are designed to prevent the passage of particles through the partitions. The apparatus further comprises a third partition having a third radius greater than the second radius, and with openings to allow the flow of fluid through the third partition. A second solid particle catalyst bed is disposed between the second and third partitions, and the partitions are designed to prevent the passage of particles through the partitions. The partitions are comprises of plates having a thickness sufficient to support the weight of the catalyst pressing against the partitions, and have milled slots along the axial length of the plates. While the terms 'milled' and 'milling' are often used to denote standard manufacturing techniques for forming metal plates, it is meant that the terms include any manufacturing method for forming slots, depressions, or holes in metal plates. The terms 'milled' and 'milling' are used for convenience hereinafter.

The plates used in the partitions comprise a solid particle side and a fluid side. The solid particle side has slots milled therein to a depth of between 0.1 and 0.5 times the thickness of the plate. The fluid side has slots milled therein, or holes drilled therein to a depth of between 0.5 and 0.9 times the thickness of the plate, and intersect the slots milled from the solid particle side. The slots in the fluid side have a width greater than the width of the slots in the solid particle side, or the holes drilled have a diameter greater than the width of the slots in the solid particle side.

In one configuration, the second partition comprises two sets of plates to form the partition wherein the first set has a solid side and a fluid side, and the second set has a solid side and a fluid side. The first set of plates has the solid side facing the first partition, and the fluid side facing away from the first partition. The second set of plates has a fluid side that faces the fluid side of the first set of plates and a solid side that faces the third partition. The two sets of plates provides a double partition with a gap in between the two sets of plates. These new plates provide a substantially thinner profile over the current profile wire screens and provides for increased reactor size without requiring a new reactor housing.

Other objects, advantages and applications of the present invention will become apparent to those skilled in the art from the following detailed description and drawings.

DETAILED DESCRIPTION OF THE INVENTION

With the increase in use of plastics, there is an increase in the production of the monomers for the plastics. As production is increased, the reactors for producing the monomers have increased in size. Many of the reactors become subject to physical constraints, such as the strength of materials in the reactor internals. Radial flow reactors are often harsh environments, and in addition to being harsh chemical environments, the operating conditions are severe in terms of pressure and temperature which induces tremendous stresses on the screens in radial flow reactors. Thermal cycles and the weight of the catalyst can cause buckling of the screens. Stronger screens or devices for retaining catalyst are needed.

Radial flow reactors, and cross-flow systems in general, need screens to contain the catalysts used in the reactors. While the present invention is described in terms of a reactor system, the equipment of the present invention is applicable to adsorbers, or other equipment used in contacting fluids with solids.

An improvement in the commercial styrene monomer reactors is to place two reactors in sequence with the second reactor having an additional oxidation bed before the reactants from the first dehydrogenation reactor enters the second reactor bed for dehydrogenation. Styrene monomer is produced by the dehydrogenation of ethylbenzene, and is an important precursor for the production of polystyrene and other styrenic resins such as acrylonitrile butadiene styrene. The improvement increases the capacity for producing styrene through the use of oxidative reheat technology.

Figure 1:
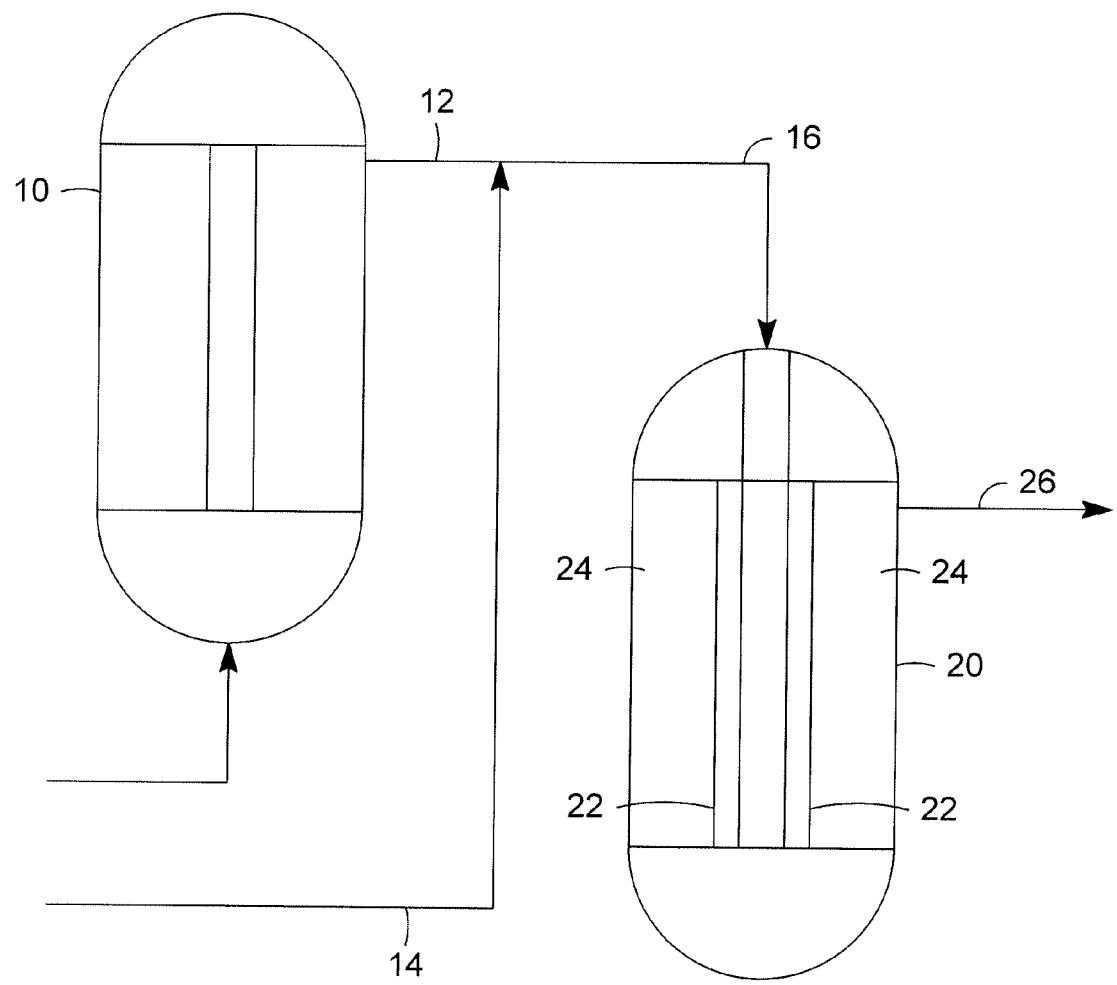
FIG. 1 shows the styrene monomer advance reactor configuration.

The process is shown in FIG. 1, where ethylbenzene is processed through a first dehydrogenation reactor 10 which generates an intermediate process stream 12 comprising ethylbenzene, styrene monomer, and hydrogen. The dehydrogenation process is endothermic and requires a substantial amount of added heat to drive the equilibrium of the reaction to efficiently generate the styrene monomer from ethylbenzene. A steam and oxygen stream 14 are added to the intermediate process stream generated by the first reactor 10, generating an intermediate mixture stream 16 and passed to a second reactor 20. The second reactor 20 comprises an oxidation catalyst bed 22 disposed in an inner annular region, and a second dehydrogenation catalyst bed 24 in an annular region surrounding the oxidation catalyst bed 22. The intermediate mixture stream 16 flows over the oxidation catalyst bed 22 prior to entering a second dehydrogenation reactor bed 24. The integration of the oxidation catalyst bed 22 with the second dehydrogenation reactor bed 24 promotes efficiency with the generation and consumption of heat needed for the process. The hydrogen in the intermediate process stream is combusted with oxygen in the oxidation catalyst bed 22, thereby generating the needed heat to drive the reaction further to completion and increasing the yield of styrene monomer. The process stream 26 exiting the second reactor 20 can be routed to a fractionation system or other separation process for the recovery of the styrene monomer. In an alternative, to increase the yields of styrene monomer, process stream 26 can be routed to either a heat exchanger and followed by another dehydrogenation reactor, or routed to another styrene monomer advanced type reactor with a bed of oxidation catalyst and a bed of dehydrogenation catalyst, similar to reactor 20.

The separation of the oxidation catalyst bed from the dehydrogenation catalyst bed uses back to back profile wire screens. The profile wire screens take up a substantial amount of volume, thereby increasing the void space and reducing the overall productivity. The apparatus of the present invention comprises a reactor having a first partition having a substantially cylindrical structure, having a first radius and forming an inner pipe where the first partition has openings for flow of a fluid through the pipe, but prevents the flow of solid particles through the pipe. The apparatus further comprises a second partition having a substantially cylindrical structure with a second radius greater than the first radius, and where the second partition has openings for the flow of fluid. A first solid particle bed is disposed between the first and second partitions. The apparatus further includes a third partition having a substantially cylindrical structure having a third radius greater than the second radius, where the third partition has openings for fluid flow. A second solid particle bed is disposed between the second and third partitions. The first and third partitions comprise plates where the plates have a solid particle side and a fluid side. The solid particle side of the plates comprise milled slots along the axial length of the plate, and the fluid side comprises milled slots along the axial length of the plates and intersect the milled slots from the solid particle side.

By use of the phrase substantially cylindrical structure, the invention is intended to include cylindrical structures, but also structures composed of individual planar components that when assembled make a multisided structure, such as having the cross sectional shape of an octagon or dodecagon, or any polygonal shaped cross-section, but can be substantially treated as a cylindrical structure.

Figure 2:
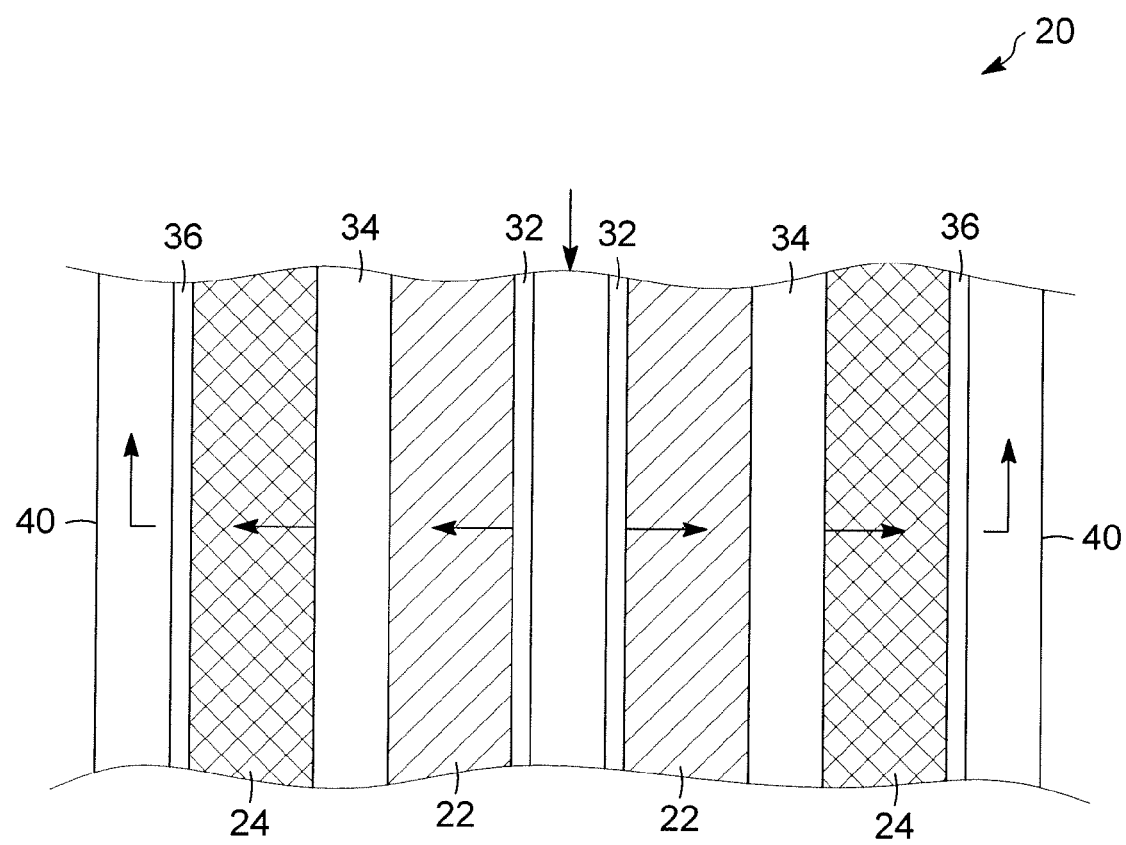
FIG. 2 shows a cross-section of the reactor with the combination of the oxidation reheat reactor and dehydrogenation reactor.

FIG. 2 presents a general horizontal cross-section of the second reactor 20. The reactor comprises a centerpipe region defined by the first partition 32, for the inlet of the intermediate process stream 16. The process stream flows through the centerpipe wall 32 and across the first solid particle bed which is an oxidation catalyst bed 22, where the hydrogen is combusted and heat is generated. The process stream continues to flow through the second partition 34 and into the second solid particle bed, which is a dehydrogenation catalyst bed 24, where the process stream continues to dehydrogenate the ethyl benzene. The process stream containing the product flows across the third partition 36 and is directed out of the reactor 20. A housing 40 for the reactor 20 contains the catalyst beds 22, 24, and the space between the third partition 36 and the housing 40 forms a channel for collecting the process stream containing the product.

Figure 3:
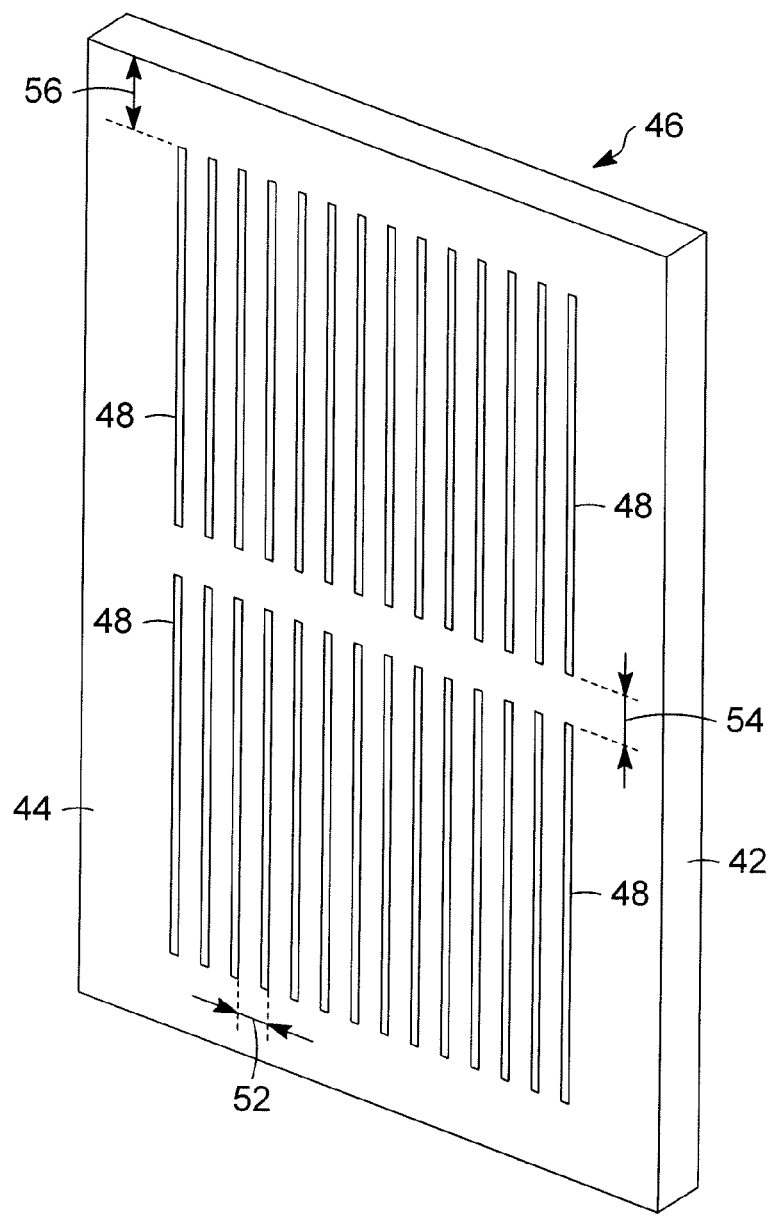
FIG. 3 shows a plate for use as part of one of the partitions in the reactor.

The partitions 32, 34 and 36, must perform the duty of preventing the passage of solid catalyst particles, while providing structural strength to hold the catalyst against the pressure of the weight of the solid particles. The partitions comprise a plurality of plates that have slots 48 milled therein. The plates 42, as shown in FIG. 3, have a solid particle side 44 and a fluid side 46. The slots 48 in the plate are milled in the solid particle side to a width of less than 1 mm, preferably with a width of less than 0.7 mm, and more preferably less than 0.5 mm. The plates 42 are further milled to have slots on the fluid side, wherein the slots in the fluid side intersect the slots 48 from the solid particle side, and the width of the slots in the fluid side have a width greater than the width of the slots in the solid particle side.

In order to maintain sufficient strength of the plate, while maximizing the openings in the plate, as shown in FIG. 3, the milled slots 48 on the solid particle side will be from 50 to 200 mm. long, and will have a spacing 52 of 1 to 5 mm apart from centerline to centerline of the slots, with a preferred spacing 52 between 2 and 5 mm. Slots, in the direction along the slots length, or longitudinally, will have a spacing 54 from 5 mm to 50 mm between the ends of the slots, and will end a distance 56 from the end of the plate between 10 and 100 mm. Preferably, the slots will be at least 100 mm long, and the longitudinal spacing 54 will be between 5 mm and 30 mm, with a distance 56 from the end of the plate between 20 mm and 40 mm.

Figure 4:
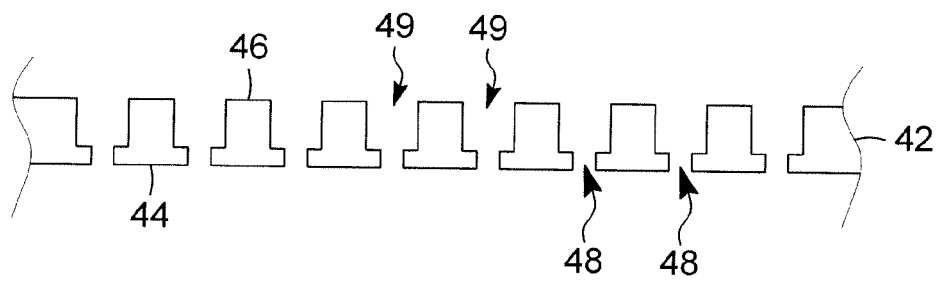
FIG. 4 shows a cross-section of the plate used in the reactor.

A cross-section of one of the plates 42 is shown in FIG. 4, showing the milled slots 48 from the solid particle side 44 intersecting the milled slots 49 from the fluid side 46. The slots 49 on the fluid side 46 are a greater depth through the plate 42 and a greater width than the slots 48 milled in the solid particle side 44. The solid particle side slots 44 have a slot width of less than 1 mm, with a preferred width of less than 0.7 mm with a more preferred width of less than 0.5 mm. The slots 48 milled from the solid particle side 44 are milled to a depth from 0.1 to 0.5 times the thickness of the plate 42. The slots 49 milled from the fluid side 49 are milled to a depth from 0.5 to 0.9 times the thickness of the plate 42.

In a preferred embodiment, the second partition 34 comprises back-to-back plates 42. The plates 42 have the fluid sides 46 face each other, and the solid particle sides 44 face away from each other, or facing the catalyst beds 22, 24. A gap of between 1 mm and 20 mm between the plates 42 of the second partition is kept to allow fines to move downward between the plates 42. The use of plates 42 facing each other to form the second partition 34 reduces the size of the space by the conventional back-to-back profile wire screens and the supports associated with the profile wire screens. This increases the volume available for the dehydrogenation reactor bed 24 without increasing the overall size of the reactor 20, and allows for increasing the capacity of the reactor 20 without replacing the entire reactor 20.

Figure 5:
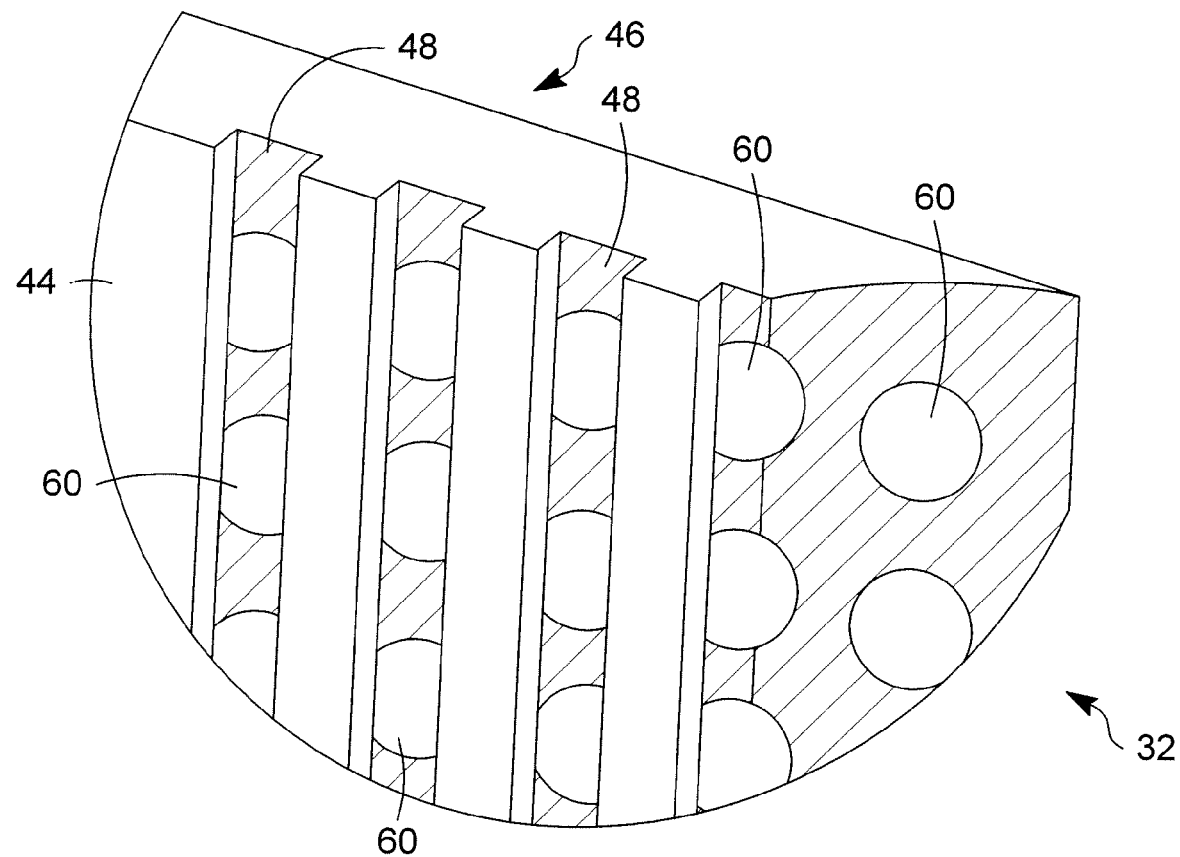
FIG. 5 shows a cut-away section of a plate comprised of milled slots in the solid particle side and drilled holes in the fluid side of the plate.

In another embodiment, the partitions 32, 34 and 36 comprise plates having a milled side and a drilled side, where a cut-away section of a plate is shown in FIG. 5. The plates 32, 34, 36 comprise a solid particle side 44 where the solid particle side comprises milled slots 48 along the axial length of the plate 32, where the milled slots are as described above. The plates 32, 34, 36 further comprise a fluid side 46, where the fluid side comprises holes 60 that have been drilled into the plate 32, 34, 36. The drilled holes 60 intersect the milled slots from the solid particle side 44, and have a diameter greater than the width of the milled slots 48. In a preferred embodiment, the drilled holes 60 have a diameter between 0.7 mm and 5.0 mm and are drilled to a depth between 0.5 and 0.9 times the thickness of the plates. In the embodiment with milled slots 48 on the solid particle side 44 and drilled holes 60 on the fluid side 46, the slots 48 are spaced between 2.5 mm and 5 mm apart from centerline to centerline of the slots 48. The holes 60 are formed in parallel lines and aligned with the slots 48 in the solid particle side 44.

In this embodiment, the second partition 34 comprises two plates, with each plate having a milled side 44 and a drilled side 46. The two plates have the drilled sides 46 facing each other, with the milled sides 44 facing solid particle catalyst beds. The two plates are separated by a distance of between 1 mm and 20 mm. Fluid flowing across the two plates flows into the gap from one plate and across the gap through the second plate to contact the second bed of solids. Any fines carried into the gap will be allowed to settle out.

In another embodiment, the third partition 36 can comprise a plurality of elongated ducts. Each duct comprise a front face, two side faces, and a rear face, and the duct cross-section has a substantially trapezoidal shape. The rear face and side faces can comprise solid faces, or comprise perforated plates that allow for the flow of fluid across the faces, but primarily the side faces and rear faces are for providing structural integrity to the ducts.

The front face comprises a plate that has a solid particle side 44 that is the side in contact with solid particles outside the duct, and a fluid side 46 that is the side facing inward to the center of the duct and in contact with fluid in the duct. The solid particle side 44 has slots 48 formed therein in a parallel manner and with the slots 48 running the length of the front face of the inlet duct. The fluid side 46 has slots 49 formed therein, which pass part of the distance through the plate and intersect with the slots 48 from the solid particle side, thereby allowing fluid to flow through the front face by flowing into the fluid side slots 49, passing to the solid particle side slots 48. The solid particle side slots 48 are sized to prevent the passage of solid particles through the front face, and have a width of less than 1.0 mm, and preferably less than 0.7 mm. The fluid side slots 49 have a width greater than the solid particle side slots 48.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. An apparatus for advanced reactor technology comprising:
    a first partition having a cylindrical structure, having a first radius and forming an inner pipe, wherein the first partition has openings for the flow of fluid through the openings;
    a second partition having a cylindrical structure, having a second radius greater than the first radius, wherein the second partition has openings for the flow of fluid through the openings;
    a third partition having a cylindrical structure, having a third radius greater than the second radius, wherein the third partition has openings for the flow of fluid through the openings;
    a first bed of solid particulate matter disposed between the first partition and the second partition; and
    a second bed of solid particulate matter disposed between the second partition and the third partition;
    wherein the first and third partition comprise a plurality of plates arrayed in a circumferential manner, wherein each of the first and third plates have a solid particle side and a fluid side, and the solid particle side comprises milled slots along the axial length of the plate and the fluid side comprises milled slots or drilled holes that intersect the milled slots from the solid particle side.

2. The apparatus of claim 1 further comprising a cylindrical housing having a radius greater than the third radius, wherein the housing is impermeable to the flow of fluid.

3. The apparatus of claim 1 wherein the first bed of solid particulate matter comprises a catalyst for combustion of residual hydrogen in the fluid stream.

4. The apparatus of claim 1 wherein the second bed of solid particulate matter comprises a catalyst for dehydrogenation.

5. The apparatus of claim 1 wherein the milled slots in the solid particle side of the plates have a width less than 0.7 mm.

6. The apparatus of claim 5 wherein the milled slots in the solid particle side of the plates have a width less than 0.5 mm.

7. The apparatus of claim 1 wherein the milled slots of the fluid side of the plates in the first partition and the third partition have a greater width than the milled slots of the solid particle side of the plates.

8. The apparatus of claim 1 wherein the second partition comprises a plurality of plates arrayed in a circumferential manner, and wherein the plates have milled slots formed therein.

9. The apparatus of claim 1 wherein the second partition comprises a plurality of plates arrayed in a circumferential manner, and wherein each plate comprises milled slots having a slot width of less than 0.7 mm, and wherein the slots extend through the thickness of the plate.

10. The apparatus of claim 1 wherein the second partition comprises two sets of plates, where each set is arrayed in a circumferential manner, and where each set comprises plates having milled slots, and where each plate comprises a solid particle side and a fluid side, and wherein the fluid sides of each set face each other, thereby forming a gap between the two sets of plates.

11. The apparatus of claim 10 wherein the plates comprise milled slots in the solid particles side having a width of less than 0.7 mm, and wherein the slots on the fluid side have a width greater than the slots on the solid particle side.

12. The apparatus of claim 11 wherein the slots in the solid particle side extend to between 0.1 and 0.5 times the thickness of the plates and the slots in the fluid side extend to between 0.5 and 0.9 times the thickness of the plates.

13. The apparatus of claim 2 wherein the third partition comprises
a plurality of elongated ducts comprising a front face, two side faces, and a rear face, having a substantially trapezoidal cross-sectional shape and wherein the front face comprises the milled plate comprising a solid particle side having solid particle side slots formed therein in a parallel manner and a fluid side having fluid side slots formed therein and where the second slots intersect the first slots to allow for the passage of fluid through the plate, and wherein the plurality of elongated ducts are arrayed circumferentially around inside of the cylindrical housing.

14. The apparatus of claim 1 wherein the plates comprise a solid particle side and a fluid side, and where the solid particle side comprises milled slots along the axial length of the plate and the fluid side comprises drilled holes that intersect the milled slots from the solid particle side, and where the drilled holes have a diameter that is greater than the width of the milled slots.

15. The apparatus of claim 14 wherein the holes in the milled plate fluid side are formed in parallel lines and aligned with the slots in the solid particle side.

16. The apparatus of claim 14 wherein the holes in the second side have a diameter of less than 5.0 mm.

17. The apparatus of claim 14 wherein the slots in the first side are spaced between 2.5 and 5 mm apart.

* * * * *